United States Patent [19]

Hall

[11] Patent Number: 5,498,157
[45] Date of Patent: Mar. 12, 1996

[54] DENTAL COLOR MIXTURE INDICATOR DEVICE

[76] Inventor: Neil R. Hall, 14 Kintore Street, Wahroonga, New South Wales 2076, Australia

[21] Appl. No.: 127,265

[22] Filed: Sep. 24, 1993

[30] Foreign Application Priority Data

Oct. 7, 1992 [AU] Australia ................................. PL5165

[51] Int. Cl.⁶ ............................ A61C 19/10; A61C 13/08
[52] U.S. Cl. ........................................ 433/26; 433/203.1
[58] Field of Search .................................... 433/26, 203.1

[56] References Cited

U.S. PATENT DOCUMENTS

| | | | |
|---|---|---|---|
| 4,207,678 | 6/1980 | Jeannette | 433/203 |
| 4,657,399 | 4/1987 | Hall | 356/421 |
| 4,802,850 | 2/1989 | Boon | 433/26 |
| 4,919,617 | 4/1990 | Antons et al. | 433/26 |
| 5,114,340 | 5/1992 | Hahn | 433/26 |

FOREIGN PATENT DOCUMENTS

| | | |
|---|---|---|
| 2669526 | 5/1992 | France . |
| 2228203 | 8/1990 | United Kingdom . |

Primary Examiner—Nicholas D. Lucchesi
Attorney, Agent, or Firm—Klarquist Sparkman Campbell Leigh & Whinston

[57] ABSTRACT

A dental color mixture indicator device is described.

In an embodiment, the dental color mixture indicator device (420) comprises four component indicator devices (400–403) each retained by a common base (410). Each component indicator device (400–403) has an array of color samples (Y1-2,C1-3,R1-2) mounted to individual blades (430,440–442,450–452,460–462), with each group of blades able to be plucked from the base (410) for the purposes of a comparison with a tooth. Each color sample (Y1-2,C1-3, R1-2) corresponds with an artificial tooth material, and, on the basis of the comparison, a mixture of the respective tooth materials allows correct color matching of a restorative tooth.

The arrayed color samples (Y1-2,C1-3,R1-2), coincide with a corresponding location on a color co-ordinate system. The central colors (201) of each component indicator device (400–403) are offset from other ones of central colors with respect to the color co-ordinate system. This means a fewer number of samples are required than in the prior art to encompass the whole body of tooth color.

24 Claims, 9 Drawing Sheets

DENTAL COLOR MIXTURE INDICATOR DEVICE

FIELD OF THE INVENTION

The present invention relates to dentistry and, in particular, to an improved color mixture indicator device which finds particular application in the selection of desired artificial tooth coloring in the fabrication of bridges, crowns, partial dentures, and the like.

RELATED DISCLOSURE

The present application is related to U.S. Pat. No. 4,657, 399 issued in the name of Neil R. Hall, who is also the inventor and applicant in respect of the present application. The noted U.S. patent claims priority from Australian application No. PG3002 lodged on 23 Dec. 1983. The disclosure of the U.S. patent is incorporated herein by cross-reference.

DESCRIPTION OF THE PRIOR ART

The dental color mixture indicator device and method disclosed in the noted U.S. patent has not yet experienced any commercial success. The device is intended to assist dentists and/or dental technicians in the selection of a desired tooth color when replacing or repairing teeth or when fabricating crowns, bridges or dentures. The device also permits proper color mixing where necessary to achieve a selected color.

Figure 1:
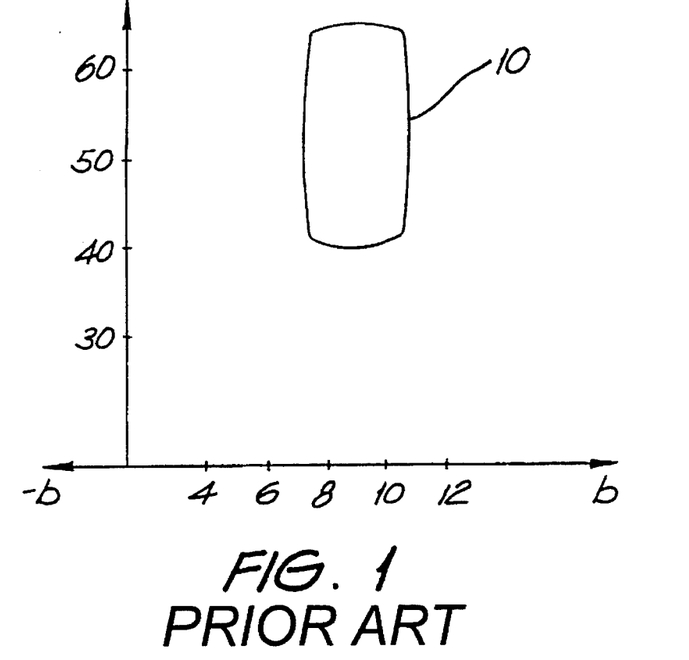
FIGS. 1 to 5 are prior art and correspond to FIGS. 1–5 of U.S. Pat. No. 4,657,399 as explained above.
Figure 2:
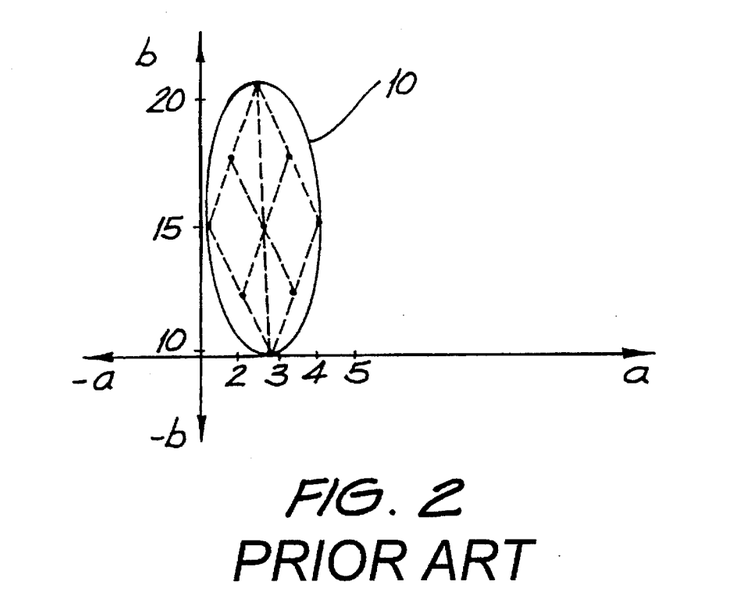
Figure 3:
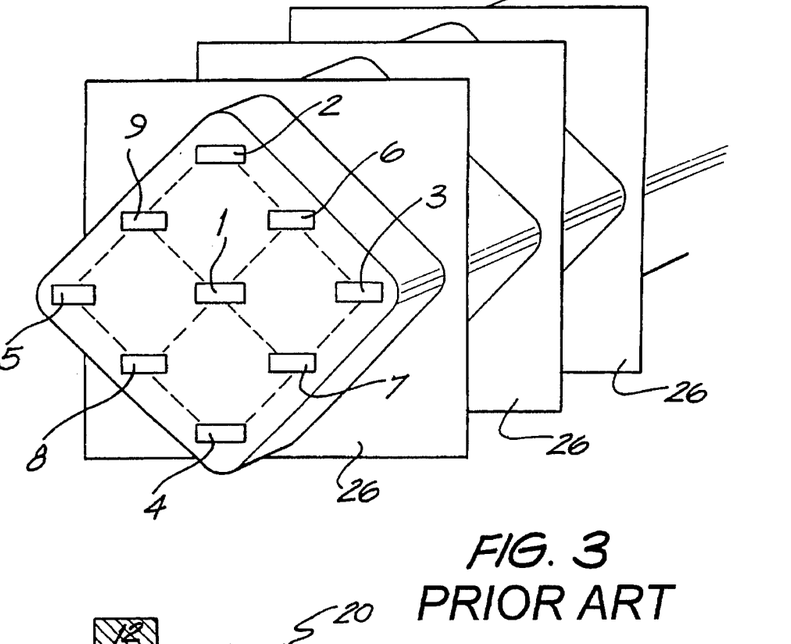
Figures 4, 5:
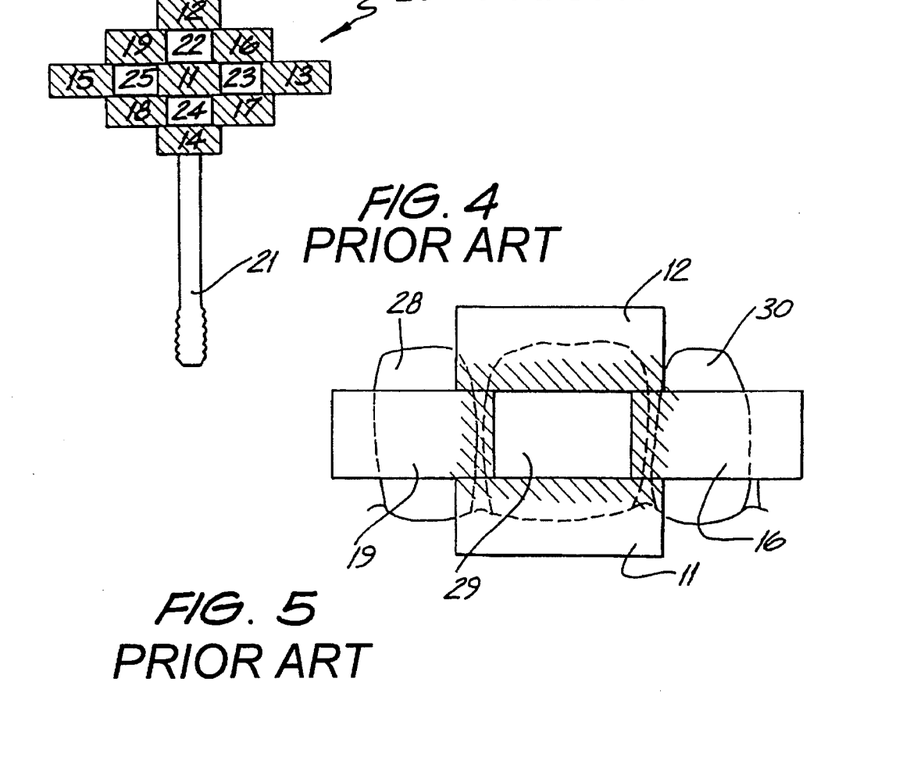

To aid in the description of the present invention, FIGS. 1–5 of the noted U.S. patent have, for convenience, been reproduced as FIGS. 1–5 of the present specification. Thus, FIG. 1 is a representation of the possible range of dental colors in a first "vertical" plane of a visual color system, FIG. 2 is a representation in a second "horizontal" co-ordinate plane of the same range of dental colors, FIG. 3 is a schematic perspective view of the color body of FIGS. 1 and 2 represented in a different co-ordinate system, FIG. 4 is a front elevation of the color mixture indicator device, and FIG. 5 illustrates how the device of FIG. 4 is held over a patient's teeth for comparison purposes, which was intended to allow part of a tooth to be viewed while the rest is obscured.

The preferred form of three-dimensional color system is a cartesian color system having a uniform color scale, such as the CIELAB psychometric color system. In this system the majority of the range of dental colors fall within a substantially ellipsoid body 10 which is illustrated in FIGS. 1 and 2. The CIELAB system represents colors in a three-dimensional cartesian co-ordinate system in which the "horizontal" chromaticity co-ordinates are designated "a" (positive representing red and negative representing green) and "b" (positive representing yellow and negative representing blue). Thus the positive and negative portions of the "horizontal" axes represent opposed colors. In this system the "vertical" axis represents luminance or lightness "L". These expressions are used interchangeably. A variant of the co-ordinate system expresses the rectangular co-ordinates "a" and "b" as polar co-ordinates "C" and "h", where "C" is the magnitude component representing chromacity and "h" is the angular component representing hue.

As can be seen in FIG. 2 a grid is superimposed on the body 10. The grid is arbitrarily chosen to cover the majority of the range of dental colors embraced by the body. The body 10 is approximated to the elongate color body shown in FIG. 3, with the intersection points of the grid (defined by the a and b axes) covering a broad range of colors; each point corresponds with one of the colors 1 to 9 shown in FIG. 3. The horizontal cuts 26 through the color body of FIG. 3 are equally spaced, and therefore represent each of the colors 1 to 9 at various discrete values of luminance, L.

It is also convenient to briefly restate the manner in which the indicator device 20 is used to match tooth color. The color mixture indicator device 20 shown in FIG. 4 has nine color samples 11 to 19 arranged in accordance with the co-ordinate system of FIG. 3 to allow correct matching of tooth color with one of the colors 1 to 9, or as a mixture of any two adjacent color samples (say, 11 and 12, or 19 and 16).

in assessing the desired color for the artificial teeth to be fabricated for a patient, it was intended that the dentist select one of the five color mixture indicator devices 20 (there being one device 20 for each of the cuts or lightness levels 26 of FIG. 3). This device would then be held against the existing or remaining teeth 28, 29 and 30 of the patient as indicated in FIG. 5. It is apparent from FIG. 5 that the size of the color samples 11 to 19 and the spaces 22 to 25, facilitate the color comparison since, for example, all the colors 2, 6, 1 and 9 of the corresponding samples 12, 16, 11 and 19 can be directly compared with the color of the tooth 29. If neither of these colors is an exact match, then an evaluation of the mixture of colors 1 and 2, for example, can be made by estimating the resultant color formed from a mixture of color samples 11 and 12.

If none of the colors of a particular device 20 appear to match the patient's teeth, then a different device 20 could be selected corresponding to a different cut 26. For each indicator device 20 of the set of indicator devices, the colors will range in chromaticity with various degrees of saturation of yellow and red in the direction from color sample 12 towards color sample 14 of the device 20.

As noted, the regular grid ascribed to the ellipsoid body 10 shown in FIG. 2 and translated onto FIG. 3 is arbitrary, and was chosen so as to cover what was thought to be the possible range of tooth coloring. The grid was centred on a=3, b=15 (with respect to the co-ordinate system), and remained so for each cut 26.

Since the issue of the noted U.S. patent it has been recognised by the inventor that 80% of all tooth colors are matchable to the three central colors samples 11, 12 and 14, or combinations of adjacent color samples 16–19. This unexpectedly leads to a simplification, since the inventor has now realised that it is possible to eliminate the extreme side color samples 13 and 15, thereby decreasing the cost of the devices to the user, and meaning that the user can stock a smaller range of tooth restorative materials.

On further investigation, the inventor discovered that the ellipsoid body 10 representing the assumed range of all tooth colors under the CIELAB system (as represented in FIG. 2) was actually constituted by a series of narrower ellipsoids located at different luminance levels, and that previous assumptions about the range and nature of tooth colors were incorrect. The reason for the false assumptions appears to be that the correct tooth color volume represented by these narrower ellipsoids tended to blend into the one larger ellipsoid 10 when notionally viewed from above the a–b plane, for reason of actually viewing hue shifts, and seeking to bound all those hue values over the presumed luminance range.

Upon further investigation it was realised by the inventor that as the central color 1 was varied in luminance (darkened or lightened) the hue shift was quantifiable, which the inventor has now determined to be approximately 3 degrees of h for every five units of luminance, L.

A further discovery was made by selection of the central color 1 for each cut 26 or luminance level to be plus or minus three degrees of the central color of an adjacent cut 26. Under these restricted conditions up to 95% of all tooth colors could be reproduced by only the three central colors 1, 2 and 4. It was also discovered that it would now be possible to apply a further restriction of only four cuts 26, each one corresponding to a spacing of five units of L, in order to cover the desired 15–20 unit range. Consequently, only four devices 20 are required, and the set of color materials needed to be stocked by manufacturers and suppliers can be reduced.

The present invention takes advantage of these important discoveries.

SUMMARY OF THE INVENTION

Therefore, according to one aspect of the invention, there is disclosed a set of dental color mixture indicator devices comprising a plurality of component indicator devices, each said component indicator device having a plurality of color samples located in an array and arranged about a central one of the color samples with each sample spaced apart from samples adjacent thereto, the colors of said samples being representative of colors of a predetermined color system having a co-ordinate system aligned with said array wherein the color of each of said samples corresponds to the color of the corresponding location in said co-ordinate system, the colors of the samples of each said component device being located on a plane of said co-ordinate system and the plane corresponding to each device being substantially parallel to, and spaced from, the planes of the other ones of said component devices and such that the central color samples of adjacent planes are offset with respect to the co-ordinate system, and whereby, in use of the said set, a patient's tooth can be compared against any one of said component devices and a desired dental color intermediate a selected pair of said color samples can be mixed for fabrication by a mixture of the coloring materials used to fabricate said selected pair.

According to another aspect of the invention, there is disclosed a dental color mixture indicator device comprising a plurality of component devices, each of said component devices having a plurality of color samples located in an array and arranged about a central one of the color samples with each sample spaced apart from samples adjacent thereto, the colors of said samples being representative of colors of a predetermined color system having a co-ordinate system aligned with said array wherein the color of each of said samples corresponds to the color of the corresponding location in said co-ordinate system, the colors of the samples of each said device being located on a plane of said co-ordinate system and the plane corresponding to each device being substantially parallel to, and spaced from, the planes of the other ones of the component devices and such that the central color samples of adjacent planes are offset with respect to the co-ordinate system, and whereby, in use of the indicator device, a patient's tooth can be compared against any one of said component devices and a desired dental color intermediate a selected pair of said color samples can be mixed for fabrication by a mixture of the coloring materials used to fabricate said selected pair.

According to a further aspect of the invention, there is disclosed a method of selecting a dental color from an elongate body of possible dental colors represented on a color co-ordinate system, said body having a longitudinal axis, and said method comprising the steps of notionally cutting said body at points along said axis with a plurality of substantially parallel cuts, notionally locating a regular grid of lines on each of said cuts, said lines having intersections forming an array of locations arranged about a central location, selecting a plurality of color samples for each cut, each of said color samples corresponding to a color lying at a corresponding intersection location of the grid on said cut, the central one of the color samples for adjacent cuts being coincident on the longitudinal axis of the body but offset with respect to an axis normal to the plane of the said parallel cuts, and selecting a desired shade of said dental color by firstly selecting one of said cuts, and secondly selecting the desired shade to be either one of said selected color samples for the selected cut or a color mixture of at least two adjacent ones of said selected color samples for the selected cut.

According to yet a further aspect of the invention, there is provided a method of enabling selection of a dental color from an elongate body of possible dental colors represented on a color co-ordinate system, said body having a longitudinal axis, and said method comprising the steps of notionally cutting said body at points along said axis with a plurality of substantially parallel cuts, notionally locating a regular grid of lines on each of said cuts, said lines having intersections forming an array of locations arranged about a central location, and selecting a plurality of color samples for each cut, each of said color samples corresponding to a color lying at a corresponding intersection location of the grid oil said cut, the central one of the color samples for adjacent cuts being coincident on the longitudinal axis of the body but offset with respect to an axis normal to the plane of the said parallel cuts so as to enable the subsequent selection of a desired shade of said dental color.

According to a still further aspect of the present invention, there is disclosed a set of dental color materials from which artificial tooth material can be fabricated from either one of said dental color materials or a color mixture of only two of said dental color materials, said set of dental color materials enabling substantially all the range of naturally occurring tooth colors to be fabricated, said set of dental color materials comprising a plurality of colors selected from an elongate body of possible dental colors represented on a color co-ordinate system and having a longitudinal axis, by notionally cutting said body at points along said axis with a plurality of substantially parallel cuts, notionally locating a regular grid of lines on each of said cuts, said lines having intersections forming an array of locations including a central location, and selecting a plurality of color samples for each cut, each of said color samples corresponding to a color lying at a corresponding intersection location of the grid on said cut, the central one of the color samples for adjacent cuts being coincident on the longitudinal axis of the body but offset with respect to an axis normal to the plane of the said parallel cuts.

Preferably, an artificial tooth can be fabricated from a color mixture of two of said dental color materials lying in a vertical plane of the said grid and two of said dental color materials lying in a horizontal plane of said grid.

Preferably there are four cuts spaced apart by 5 units of L and three color samples per plane or cut so that the abovementioned set of dental color materials has only 4×3=12 members. This represents a very substantial reduction in the current range of dental colors required to fabricate an adequate range of tooth colors which typically encompasses 50–100 color materials. The preferred offset is in the range of from 2–4 degrees of hue towards the red for each 4–6 unit decrease in luminance.

According to yet another aspect of the invention, there is disclosed a color guide for selection of artificial tooth material from which artificial teeth can be fabricated, the color guide enabling substantially all the range of naturally occurring tooth colors to be selected for fabrication, said set of dental color materials comprising a printed color representation of a plurality of colors selected from an elongate body of possible dental colors represented on a color co-ordinate system and having a longitudinal axis, by notionally cutting said body at points along said axis with a plurality of substantially parallel cuts, notionally locating a regular grid of lines on each of said cuts, said lines having intersections forming an array of locations including a central location, and selecting for each cut a plurality of colors, each of said-colors lying at a corresponding intersection location of the grid on said cut, the central one of the color samples for adjacent cuts being coincident on the longitudinal axis of the body but offset with respect to an axis normal to the plane of the said parallel cuts.

According to one other aspect of the invention, there is disclosed a worksheet for assisting in the prescription of artificial tooth material from which artificial teeth can be fabricated, the worksheet displaying a grid for each of said planes as referred to above, and whereby, in use of a device referred to above, the resulting proportional combination of adjacent vertical color samples and adjacent horizontal samples is noted on the worksheet, the worksheet then being provided as a reference from which artificial tooth material can be mixed to achieve the desired matching tooth color for a tooth to be replaced or restored.

BRIEF DESCRIPTION OF THE DRAWINGS

Preferred embodiments of the invention will now be described with reference to the drawings, in which.

DESCRIPTION OF PREFERRED EMBODIMENTS

Figure 6:
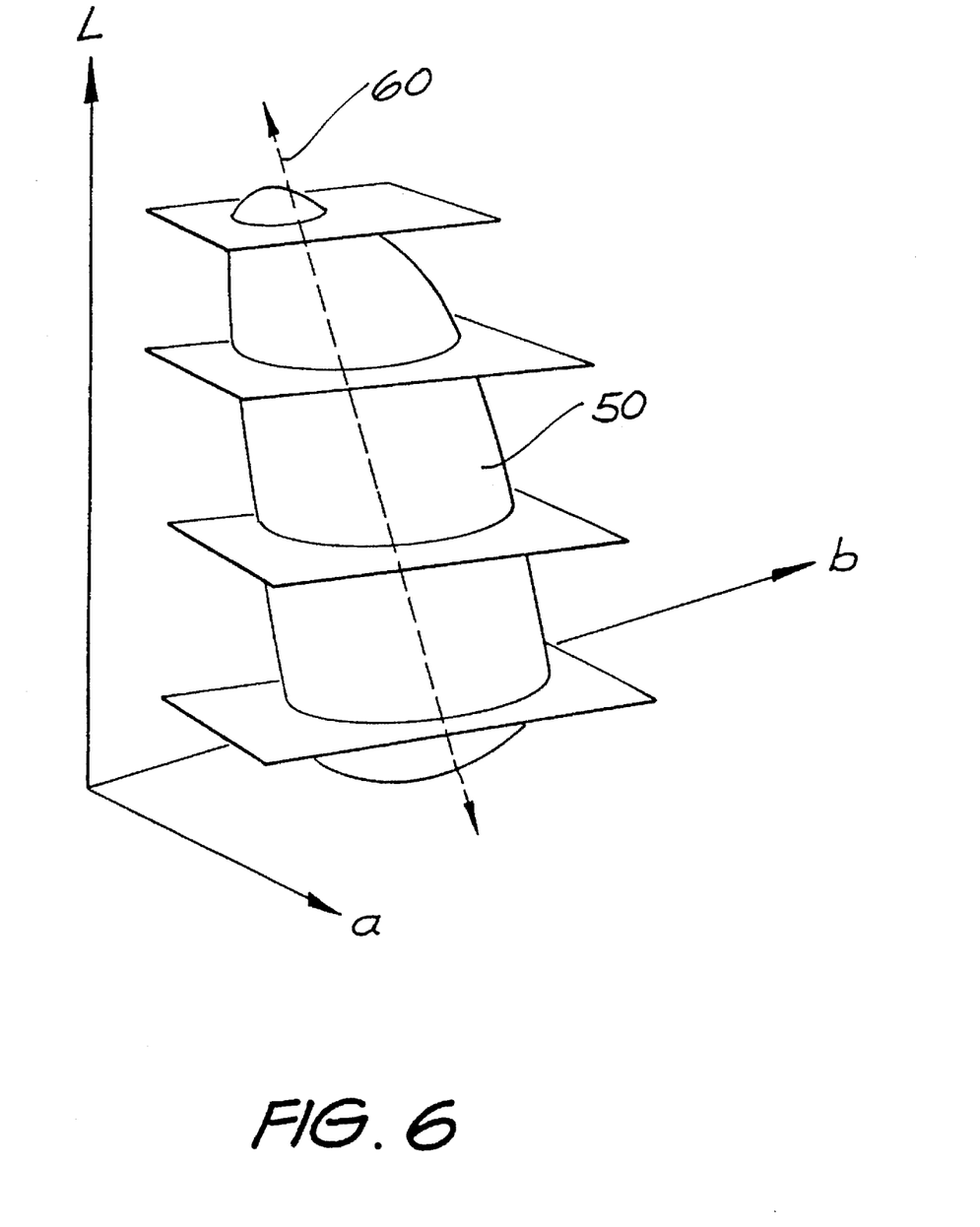
FIG. 6 is a representation of the color body of all tooth colors when mapped under the CIELAB system.

It will be appreciated from FIGS. 2 and 3 that the body of all tooth colors was previously assumed to be a regular elongate ellipsoidal body 10 having a longitudinal axis normal to the a and b axes. As has now been discovered, the body of tooth colors is less regularly shaped, and constituted by a narrower ellipsoid. FIG. 6 shows the color body 50 in a 3-dimensional representation mapped against the a, b and L axes under the CIELAB system. The body covers a 15–20 unit range in luminance, the range of "a" values is approximately 5 units whilst the range of "b" values remains about 10 units as previously thought to be.

Figure 7:
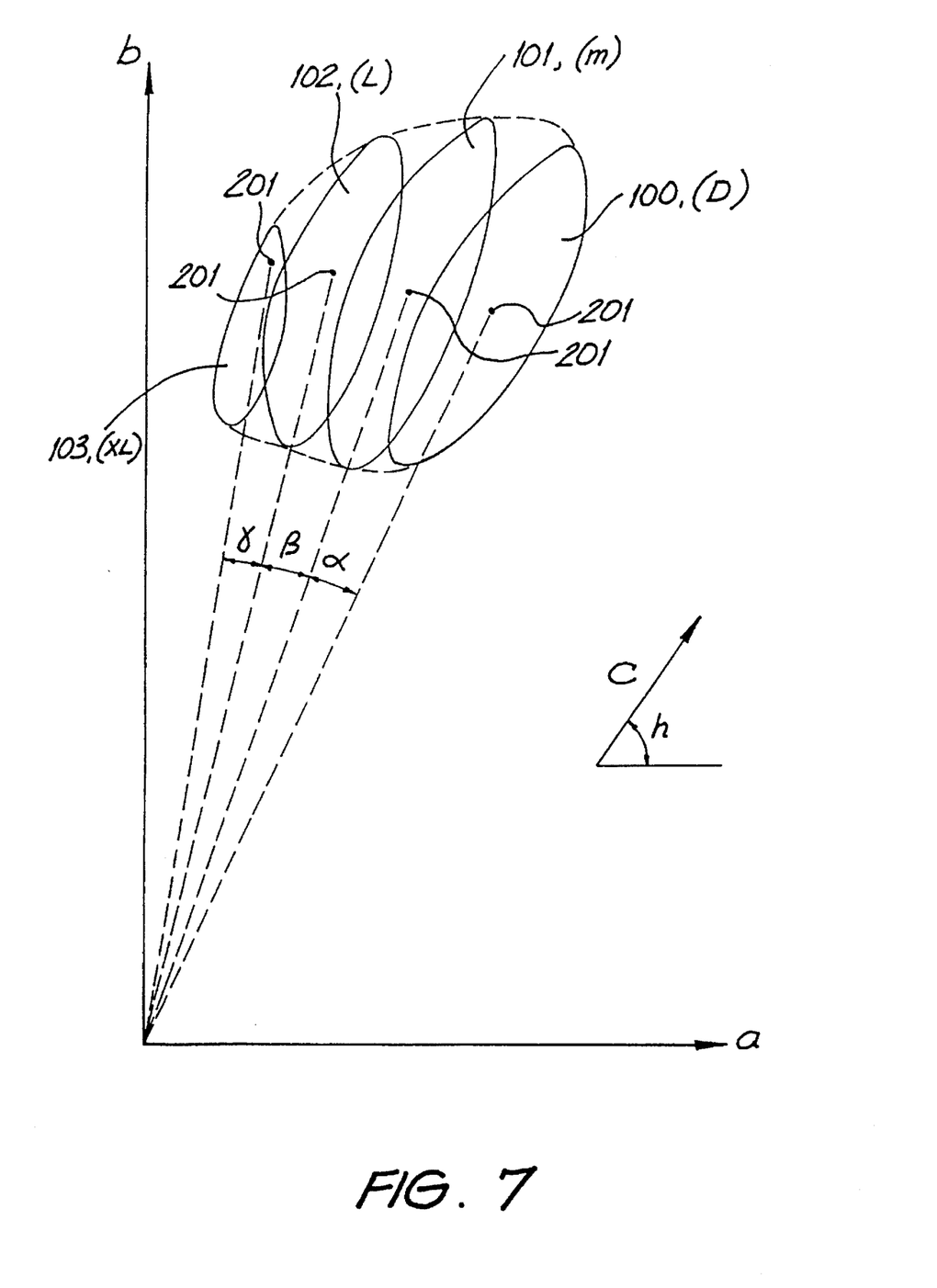
FIG. 7 is a representation of the color body at each slice or luminance level mapped onto the a and b axes.

FIG. 6 also shows a longitudinally extending principal axis 60 for the body 50, which lies generally in the L plane. The principal axis 60 is at an angle with respect to the normal of the a–b plane. The body 50 has notional cuts or slices, identified as D, M, L and XL, made parallel to the a–b plane at equally spaced points along the principal axis 60. When the four ellipsoids that result from the cuts D–XL are viewed in cross-section, and superimposed onto the a and b axes, as shown in FIG. 7, their relative offset between the centre point 20 becomes more recognisable. That is, the angular offsets in hue (h) $\alpha$, $\beta$, $\gamma$ can be seen to be equal. The dashed outlined generally represents the locus of all a and b values taken by the color body over the range of L values. This locus approximates the color body 10 as it was previously thought to be. As previously noted, the present inventor realised that what actually was being observed was phase shifts which tended to smear the narrow ellipsoid body 50 into one larger ellipsoid 10.

Figure 8:
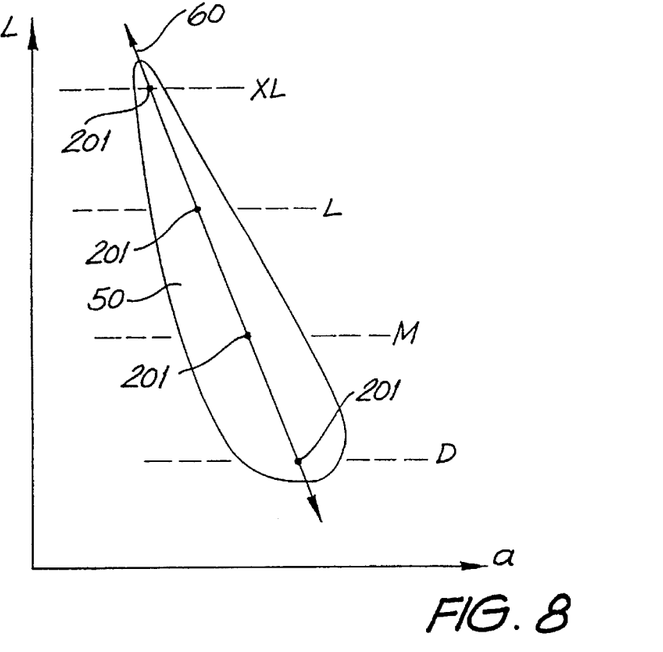
FIG. 8 is a representation of the locus of the range of "a" values (red to green) with respect to luminance.
Figure 9:
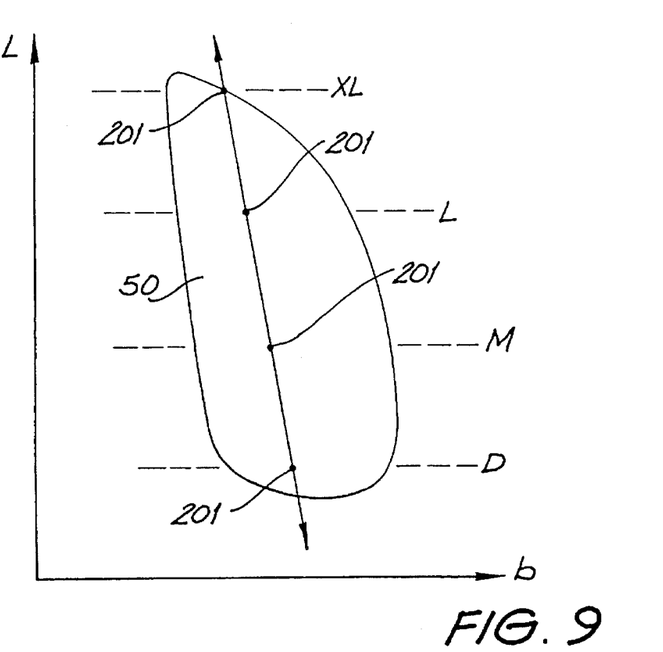
FIG. 9 shows a representation of the locus of the range of "b" values (yellow to blue) with respect to luminance.

A centre point or color 201 is again shown for each ellipsoid. This centre color 201 is chosen to lie on the principal axis 60, as can be more clearly seen in FIGS. 8 and 9. FIG. 8 shows how the centre colors 201D–201XL become less red as luminance increases (i.e. the positive a value reduces with increasing L). This shift has been quantified by the inventor as a three degree hue shift for every 5 luminance units, in which case only four cuts are required to embrace the desired 15–20 unit luminance range. The centre colors 201D–201XL sited on the principal axis 60 at each cut D–XL represent an approximate three degree hue shift for each luminance level. Therefore, the four cuts D–XL are parallel with respect to the plane of the a and b axes, and the central colors 201D–201XL are offset from one another by three degrees with respect to the L axis.

Figure 10:
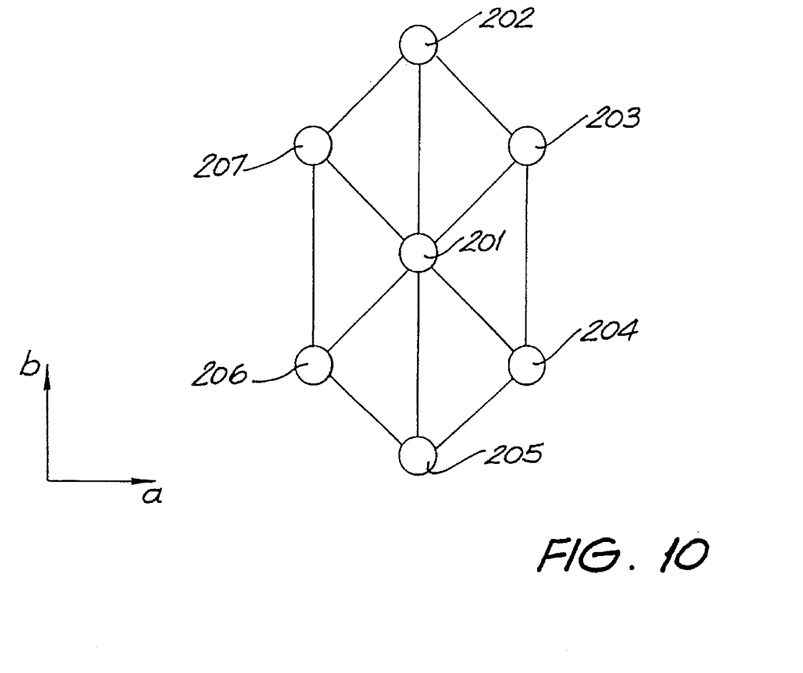
FIG. 10 is a representation of a co-ordinate system in one embodiment.

FIG. 10 shows the chosen co-ordinate system centred about the centre color 201. The grid of the co-ordinate system is sized to map onto the area of each individual ellipsoid 100 to 103 with respect to the a and b axes. The colors at the intersection of the grid of the co-ordinate system are identified by the numerals 201 to 207. The distance between any two adjacent colors in the b plane (i.e. the 'height' of the grid) is approximately 5 units, whilst the distance between adjacent colors in the a plane (i.e. one half of the 'width' of the grid) is about 2.5 units.

Figure 11:
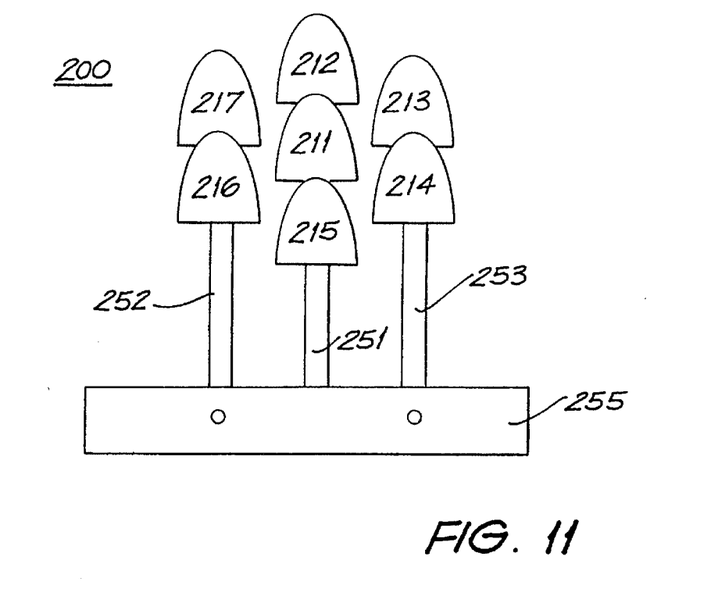
FIG. 11 is a front elevation of a color mixture indicator device constructed in accordance with a first embodiment.

FIG. 11 shows a color mixture indicator device 200 which has color samples 211–217 as would be constructed from a particular tooth restorative material and which correspond to the colors 201–207. The shape of the color samples may be tooth-like as shown, but could also be other shapes, and for example, circular. Typically a set of the devices 200 comprises four devices of the same configuration, each one representing a one of the cuts, and with a three degree hue shift between central color samples of adjacent ones of the devices. The operation of the color mixture indicator device 200 is the same as previously described in U.S. Pat. No. 4,657,399 in that a tooth can be matched with one of the color samples 211 to 217, or to fall between adjacent ones of those color samples; for example, between samples 216 and 214, or samples 211 and 212. The device 200 is constructed of three metal blades or handles 251 to 253 (hereafter blades), to which each has two or three color samples affixed to the free end. The outer blades 252 and 253 are pivotably mounted to a base 255 so that, optionally, they can be swung out of the way of the central blade 251 to enable better access in matching the tooth color with only the three central color samples 211, 213 and 215 mounted on the central handle 251.

Figure 12:
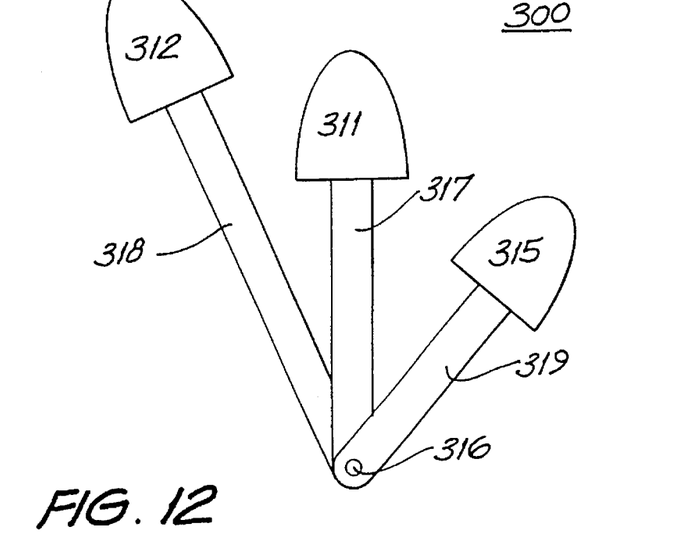
FIG. 12 is a front elevation of a color mixture indicator device of a further embodiment.

Another embodiment of an indicator device 300 is shown in FIG. 12. This device has been modified to provide only the central three color samples 311, 312 and 314, with each being mounted on an individual blade 317–319. The three separate blades are pivotably fastened to each other at one end 316. This device 300 is most suitable for the XL luminance level, for which it is believed there is only a very small range of a and b values (see FIGS. 7 and 8). It can, however, also be used for the D, M and L levels if tooth color matching is less crucial, for example, in fabricating composite restorations.

Figure 13:
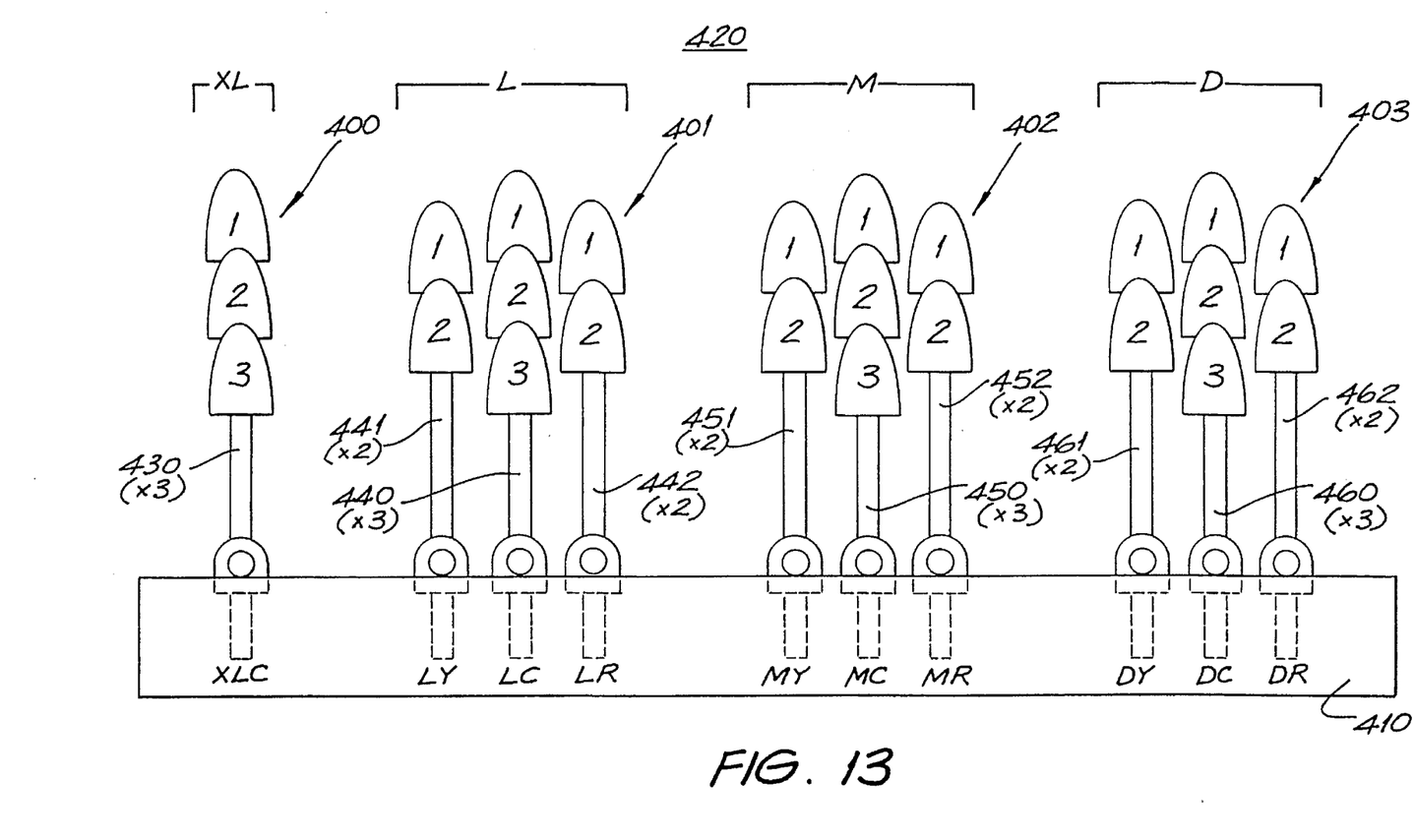
FIG. 13 is a front elevation of a set of color mixture indicator devices in accordance with another embodiment.

FIG. 13 shows another embodiment of a color mixture indicator device 420 which constitutes a complete set of devices 400–403 for each luminance level mounted on a common base 410. Each central or side group of samples for each individual device 400 plugs into, and is retained by the base. The samples are each mounted on an individual blade 430, 440–442, 450–452, 460–462, and again, each group of samples is pivotably interconnected. This means each group of blades and samples can be used in a fan-like manner. The samples at the end of each blade are also rotatable in the plane of the blade so the sample can be oriented with a tooth against which it is being compared. The individual devices 400 identified as D, M and L are generally similar to the device 200 shown in FIG. 11, while the device indentified as XL is equivalent to the device 300 shown in FIG. 12.

Each device 400–403 uniquely identifies each color sample as shown. The left side samples are more 'red' than the right sample which are respectively more 'yellow', hence the use of "Y" and "R". Clearly "C" refers to the central color samples.

In use, the samples of the device 420 are to be held at arms length adjacent the tooth to be matched to adjudge the appropriate lightness/luminance level. It is important to view the samples at arms length, as the human eye can only effectively detect variations in luminance at that distance. The eye cannot make correct distinctions of relative luminance at distance closer than arms length. Therefore each central three blades and samples for the four luminance levels are plucked out of the base 410 in turn to determine the correct luminance level.

It is then necessary to determine where the tooth color to be matched lies with respect to the three central vertical color samples. Say the "M" luminance level has been selected, in which case a tooth is then compared against samples MC1, MC2, MC3 to determine which two samples it falls between. This represents a decision as to the yellow/blue color mix in the tooth color. It is possible to estimate a proportion of, say, MC1 and MC2, to be, for example, 25% MC1 and 75% MC2. That estimation is then marked on the work sheet shown in FIG. 14.

Figure 14:
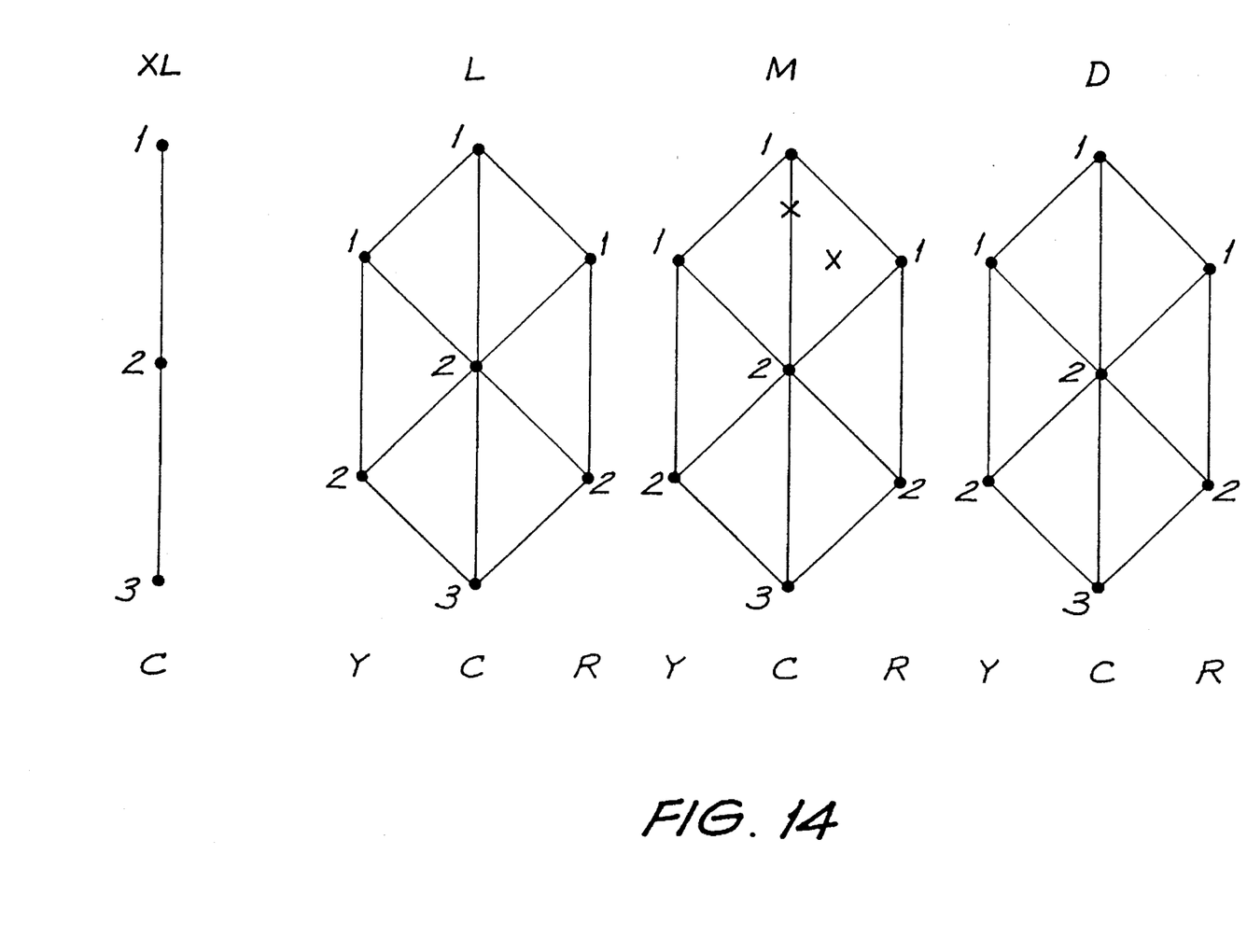
FIG. 14 illustrates how the embodiment of FIG. 13 can be utilised in conjunction with a worksheet to construct an artificial tooth, or repair an existing tooth.

This step is then followed by considering the red/green color mix by bringing the color samples MY1 and MR1 beside the tooth. Again, it is possible to estimate the proportional mix to be, for example, 25% MY1 and 75% MR1. This estimation is then marked on the work sheet, and therefore locates the desired color accurately as the intersection of those two points. A dental technician can then simply mix up the restorative materials corresponding to MC1, MC2, ML1 and MR1 in the appropriate proportions to achieve the desired result. It is as a direct result of the allocation of the strictly spaced co-ordination system that a proportional mix as specified above with respect to 'b' axis colors and 'a' axis colors results in the required color being achieved. Manufacturers of the restorative materials can fabricate colors for the complete range of color samples based solely on the specification of each sample by the L,a,b or L,C,h co-ordinates.

It is often necessary to mix up different colors for the one tooth, as a tooth normally varies in color throughout its length, especially in patient's of middle age or older. For this purpose the worksheet shown in FIG. 14 can be supplemented with a plan of all the teeth in the mouth in appropriate views, with those views marked up as to what part of the tooth is to be restored with each particular determined mixture. The worksheet may also show only one 'grid', and the appropriate luminance level prescribed to that grid, rather than having a separate grid for each luminance level.

By using the device 410, it is possible to more accurately approximate the true tooth color in a restorative material, for reason of enabling the three co-ordinates L,a,b or L,C,h to be substantially more accurately estimated than in the prior art. Prior art systems, except for U.S. Pat. No. 4,657,399 referred to above, do not in any way arrange colors or samples in strict spaced relation to a color co-ordinate system.

A further aid to the device shown in FIG. 11, FIG. 12 and FIG. 13 is a color chart (not shown) which displays, in printed form, the color samples in like relation as the devices 200, 300, 400, and also cross-matches with restorative materials corresponding to each color sample. The restorative materials can be specified as one or more types, such as porcelain, powders or artificial teeth.

Figure 15:
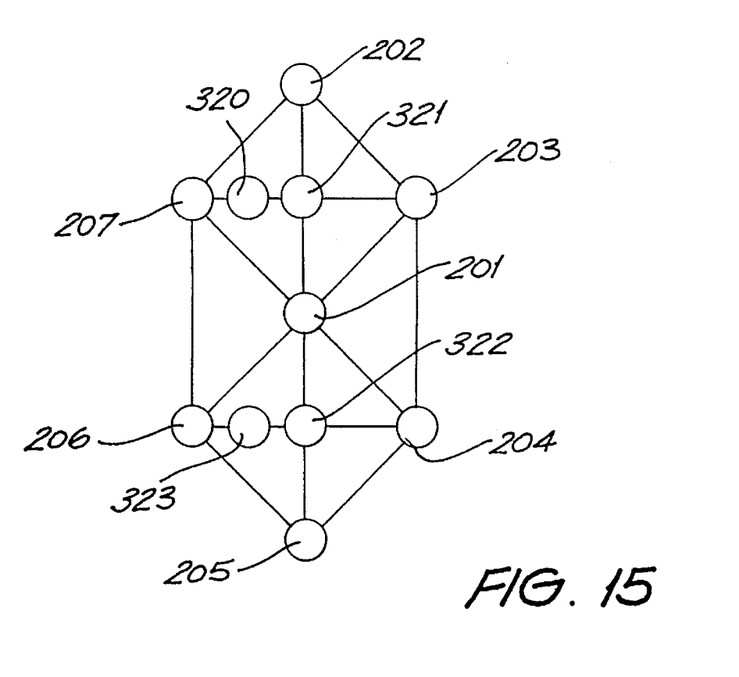
FIG. 15 is a representation of another embodiment for a co-ordinate system.

A further embodiment of the co-ordinate system shown in FIG. 15 relates to the instance where it is very important to attain as close a match of tooth color as is possible. In this case additional intermediate colors 320–323 are introduced to the existing co-ordinate system at each luminance level to enable a more detailed comparison. Even so, the principle of selecting the central colors to be offset by approximately 3 degrees in hue with respect to an adjacent cut still applies. The intermediate colors are chosen to fall between the existing colors 201–207, and their location with respect to the previously described co-ordinate system is shown in FIG. 15. Although not specifically illustrated, clearly a color mixture device embracing the colors 201–207 and 320–323 could be constructed on similar lines to that shown in FIG. 11 or FIG. 13.

It can therefore be seen that the invention provides an improved system for matching tooth color, which, by appropriate selection of the central color for each luminance level in accordance with a determined relation of hue shift with respect to luminance, results in a reduction in the number of color samples, matching devices and dental materials needed to be stocked. This had advantages for both the manufacturer of the tooth restorative materials and matching devices, and to dentists and/or dental technicians who can still ensure a high percentage of match of tooth color but at a lesser expense to themselves and their patients.

The foregoing describe only some embodiments of the present invention, and modifications, obvious to those skilled in the art, can be made thereto without departing from the present invention.

I claim:

1. A set of dental color mixture indicator devices comprising a plurality of component indicator devices, each said component indicator device having a plurality of color samples located in an array and arranged about a central one of the color samples with each sample spaced apart from samples adjacent thereto, the colors of said samples being representative of colors of a predetermined color system having a co-ordinate system aligned with said array wherein the color of each of said samples corresponds to the color of the corresponding location in said co-ordinate system, the colors of the samples of each said component device being located on a plane of said co-ordinate system and the plane corresponding to each device being substantially parallel to, and spaced from, the planes of the other ones of said component devices and such that the central color samples of adjacent planes are offset with respect to the co-ordinate system, and whereby, in use of the said set, a patient's tooth can be compared against any one of said component devices and a desired dental color intermediate a selected pair of said color samples can be mixed for fabrication by a mixture of the coloring materials used to fabricate said selected pair.

2. A set of dental color mixture indicator devices as claimed in claim 1, comprising a plurality of blades each having a first end and a second end, the color samples of at least one of the component indicator devices in the said set being fixed to said first ends of said blades, and means providing a common connection at the second ends of the blades.

3. A set of dental color mixture indicator devices as claimed in claim 2, wherein the common connection is formed by a base.

4. A set of dental color mixture indicator devices as claimed in claim 2, wherein the common connection is formed by a pivoting fastener so that the blades are arranged in the shape of a fan.

5. A set of dental color mixture indicator devices as claimed in claim 2, wherein a first number between one and three inclusive of color samples are arranged on each of a second number between one and three inclusive of blades forming each component indicator device in the said set.

6. A set of dental color mixture indicator devices as claimed in claim 2, wherein there are at least three color samples per component indicator device and four said component devices in the said set.

7. A set of dental color mixture devices as claimed in claim 1, wherein the said co-ordinate system is the CIELAB system, and the said offset is approximately 3 degrees in hue towards red for each adjacent plane in a direction of decreasing luminance.

8. In combination with the set of dental color mixture indicator devices of claim 1, a worksheet for assisting in the prescription of artificial tooth material from which artificial teeth can be fabricated, the worksheet displaying a plurality of grids for each plane for noting the resulting proportional combination of adjacent vertical color samples and adjacent horizontal samples on the worksheet, whereby the worksheet provides a reference from which artificial tooth material can be mixed to achieve the desired matching tooth color for a tooth to be replaced or restored.

9. A dental color mixture indicator device comprising a plurality of component devices, each of said component devices having a plurality of color samples located in an array and arranged about a central one of the color samples with each sample spaced apart from samples adjacent thereto, the colors of said samples being representative of colors of a predetermined color system having a co-ordinate system aligned with said array wherein the color of each of said samples corresponds to the color of the corresponding location in said co-ordinate system, the colors of the samples of each said device being located on a plane of said co-ordinate system and the plane corresponding to each device being substantially parallel to, and spaced from, the planes of the other ones of the component devices and such that the central color samples of adjacent planes are offset with respect to the co-ordinate system, and whereby, in use of the indicator device, a patient's tooth can be compared against any one of said component devices and a desired dental color intermediate a selected pair of said color samples can be mixed for fabrication by a mixture of the coloring materials used to fabricate said selected pair.

10. A dental color mixture indicator device as claimed in claim 9, wherein the color samples of each component device are fixed to an end of a blade and the other end of each blade of each component device is connected to a common base of the dental color mixture indicator device.

11. A dental color mixture indicator device as claimed in claim 10, wherein a first number between one and three inclusive of color samples are arranged on each of a second number between one and three inclusive of blades forming each component device.

12. A dental color mixture indicator device as claimed in claim 10, wherein there are at least three color samples per component device and four said component devices comprise the dental color mixture indicator device.

13. A dental color mixture indicator device as claimed in claim 9, wherein the said co-ordinate system is the CIELAB system, and the said offset is approximately 3 degrees in hue towards red for each adjacent plane in a direction of decreasing luminance.

14. A method of selecting a dental color from an elongate body of possible dental colors represented on a color co-ordinate system, said body having a longitudinal axis, and said method comprising the steps of:

notionally cutting said body at points along said axis with a plurality of substantially parallel cuts;

notionally locating a regular grid of lines on each of said cuts, said lines having intersections forming an array of locations arranged about a central location;

selecting a plurality of color samples for each cut, each of said color samples corresponding to a color lying at a corresponding intersection location of the grid of said cut, the central one of the color samples for adjacent cuts being coincident on the longitudinal axis of the body but offset with respect to an axis normal to the plane of the said parallel cuts; and selecting a desired shade of said dental color by firstly selecting one of said cuts, and secondly selecting the desired shade to be either one of said selected color samples for the selected cut or a color mixture of at least two adjacent ones of said selected color samples for the selected cut.

15. A method as claimed in claim 14, wherein the said co-ordinate system is the CIELAB system, and the said offset approximately 3 degrees in hue towards red for each adjacent cut in a direction of decreasing luminance.

16. A method of enabling selection of a dental color from an elongate body of possible dental colors represented on a color co-ordinate system, said body having a longitudinal axis, and said method comprising the steps of:

notionally cutting said body at points along said axis with a plurality of substantially parallel cuts;

notionally locating a regular grid of lines on each of said cuts, said lines having intersections forming an array of locations arranged about a central location; and selecting a plurality of color samples for each cut, each of said color samples corresponding to a color lying at a corresponding intersection location of the grid on said cut, the central one of the color samples for adjacent cuts being coincident on the longitudinal axis of the body but offset with respect to an axis normal to the plane of the said parallel cuts so as to enable the subsequent selection of a desired shade of said dental color.

17. A set of dental color materials from which artificial tooth material can be fabricated from either one of said dental color materials or a color mixture of at least two of said dental color materials, said set of dental color materials enabling substantially all the range of naturally occurring tooth colors to be fabricated, said set of dental color materials prepared by a process comprising the steps of:

notionally cutting an elongate body of possible dental colors represented on a color co-ordinate system and having a longitudinal axis at points along said axis with a plurality of substantially parallel cuts;

notionally locating a regular grid of lines on each of said cuts, said lines having intersections forming an array of locations including a central location; and selecting a plurality of colors of said set of dental color materials for each cut, each of said colors corresponding to a color lying at a corresponding intersection location of the grid on said cut, the central one of the colors for adjacent cuts being coincident on the longitudinal axis of the body but offset with respect to an axis normal to the plane of the said parallel cuts.

18. A set of dental color materials as claimed in claim 17, wherein the said co-ordinate system is the CIELAB system, and the offset is approximately 3 degrees in hue towards red for each adjacent cut in a direction of decreasing luminance.

19. A set of dental color materials as claimed in claim 18, wherein there are four cuts spaced apart by approximately five units of luminance.

20. An artificial tooth fabricated from at least one dental color material of a set of dental color materials, said set of dental color materials enabling substantially all the range of naturally occurring tooth colors to be fabricated, said set of dental color materials prepared by a process comprising the steps of:

notionally cutting an elongate body of possible dental colors represented on a color co-ordinate system and having a longitudinal axis at points along said axis with a plurality of substantially parallel cuts;

notionally locating a regular grid of lines on each of said cuts, said lines having intersections forming an array of locations including a central location; and selecting a plurality of colors of said set of dental color materials for each cut, each of said colors corresponding to a color lying at a corresponding intersection location of the grid on said cut, the central one of the colors for adjacent cuts being coincident on the longitudinal axis of the body but offset with respect to an axis normal to the plane of the said parallel cuts.

21. An artificial tooth as claimed in claim 20, wherein two of the mixed dental color materials lie adjacent in a vertical plane of the said grid and two of the mixed dental color materials lie adjacent in a horizontal plane of the said grid.

22. An artificial tooth as claimed in claim 20, wherein a color mixture of only two of said dental color materials are mixed, and wherein the two dental color materials either lie adjacent in a vertical plane of said grid or lie adjacent in a horizontal plane of said grid.

23. A color guide comprising a printed color representation of a plurality of colors for selection of artificial tooth material from which artificial teeth can be fabricated, the color guide enabling substantially all the range of naturally occurring tooth colors to be selected for fabrication, said color guide prepared by a process comprising the steps of:

notionally cutting an elongate body of possible dental colors represented on a color co-ordinate system and having a longitudinal axis at points along said axis with a plurality of substantially parallel cuts;

notionally locating a regular grid of lines on each of said cuts, said lines having intersections forming an array of locations including a central location; and selecting for each cut a plurality of colors, each of said colors lying at a corresponding intersection location of the grid on said cut, the central one of the colors for adjacent cuts being coincident on the longitudinal axis of the body but offset with respect to an axis normal to the plane of the said parallel cuts.

24. A color guide as claimed in claim 23, wherein the said co-ordinate system is the CIELAB system, and the offset is approximately 3 degrees in hue towards red for each adjacent cut in a direction of decreasing luminance.

* * * * *